(12) United States Patent
Liu

(10) Patent No.: US 7,164,038 B1
(45) Date of Patent: Jan. 16, 2007

(54) PROCESS FOR DECOLORIZING AROMATIC DICARBOXYLIC ACIDS

(75) Inventor: Zhufang Liu, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/353,815

(22) Filed: Feb. 14, 2006

(51) Int. Cl.
*C07C 51/42* (2006.01)

(52) U.S. Cl. ..................................... 562/487

(58) Field of Classification Search ............... None
See application file for complete search history.

(56) References Cited

U.S. PATENT DOCUMENTS

| | | | |
|---|---|---|---|
| 3,151,154 A | 9/1964 | Sargent et al. |
| 3,584,039 A | 6/1971 | Meyer |
| 3,726,915 A | 4/1973 | Pohlmann |
| 4,394,299 A | 7/1983 | Puskas et al. |
| 4,405,809 A | 9/1983 | Stech et al. |
| 4,415,479 A | 11/1983 | Puskas et al. |
| 4,467,110 A | 8/1984 | Puskas et al. |
| 4,892,972 A | 1/1990 | Schroeder et al. |
| 4,937,378 A | 6/1990 | Schroeder |
| 5,616,792 A | 4/1997 | Bartos et al. |
| 5,756,833 A | 5/1998 | Rosen et al. |
| 6,455,731 B1 | 9/2002 | Shigematsu et al. |

FOREIGN PATENT DOCUMENTS

WO  WO 02/06200 A1  1/2002

OTHER PUBLICATIONS

Hunter, "The Measurement of Appearance," Chapter 8, pp. 102-132, John Wiley & Sons, NY, NY (1975).
Wyszecki et al, "Color Science, Concepts and Methods, Quantitative Data and Formulae," 3d Edition, pp. 166-168, John Wiley & Sons, NY, NY (1982).

*Primary Examiner*—Paul A. Zucker
(74) *Attorney, Agent, or Firm*—Michael K. Carrier; Bernard J. Graves, Jr.

(57) ABSTRACT

In a process for reducing the visible color of a crude aromatic dicarboxylic acid containing colored contaminants, an aqueous ammonia solution of the crude aromatic dicarboxylic acid is prepared and contacted with hydrogen in a reactor in the presence of a heterogeneous metal-containing catalyst that includes a noble metal and a support. The process is carried out under conditions of temperature, pressure, and contact time effective to reduce the visible color of the aromatic dicarboxylic acid.

22 Claims, No Drawings

PROCESS FOR DECOLORIZING AROMATIC DICARBOXYLIC ACIDS

FIELD OF THE INVENTION

The present invention relates to the decolorization of aromatic dicarboxylic acids and, more particularly, to a process for reducing the visible color of such acids by catalytic hydrogenation.

BACKGROUND OF THE INVENTION

Terephthalic acid is the starting material for polyethylene terephthalate (PET), which is the principal polymer used to manufacture polyester fibers, polyester films, and resins for bottles and like containers. Crude terephthalic acid (CTA), which is produced by the direct oxidation of p-xylene by oxygen, must be purified to be useful for manufacturing high quality and low color PET, which is produced by a condensation reaction between purified terephthalic acid (PTA) and ethylene glycol. Even after initial purification, however, terephthalic acid typically contains residual amounts of colored contaminants. It is highly desirable to reduce the concentration of such remaining colored impurities prior to using the acid to produce PET.

It is known that terephthalic acid can be purifed by subjecting the crude acid to hydrogenation in the presence of a noble metal catalyst, as described, for example, in Meyer, U.S. Pat. No. 3,584,039, Stech et al., U.S. Pat. No. 4,405,809, and Pohlmann, U.S. Pat. No. 3,726,915, the disclosures of which are incorporated herein by reference. Additional descriptions of the purification of aromatic dicarboxylic patents by catalytic hydrogenation processes are included in the following patents, the disclosures of which are incorporated herein by reference:

Shigematsu et al., U.S. Pat. No. 6,455,731, discloses a three-step process for producing high-purity aromatic acids: preparing an amine salt by the reaction of crude acid with an amine, continuously decomposing the amine salt to form a slurry of crystallized acid, and separating crystals of the acid from the slurry.

Sargent et al., U.S. Pat. No. 3,151,154, discloses a process for decolorizing phthalic acids (or salts thereof) prepared by the nitric acid oxidation of xylenes or toluic acids that comprises hydrogenating the crude oxidation product in the presence of a catalyst, acidifying the mixture with a strong acid, and recovering the phthalic acid that crystallizes from solution.

Meyer, U.S. Pat. No. 3,584,039 discloses a process for preparing fiber-grade terephthalic acid by catalytic hydrogenation of a solution of impure terephthalic acid, followed by separation of the catalyst and crystallization of the purified acid, impurities being retained in the aqueous mother liquor.

The following patents, all issued to Puskas et al., relate to the purification of terephthalic acid by hydrogenation in the presence of a palladium catalyst formed by contacting a porous carbon support with an aqueous solution of a palladium salt and an amine in the presence of an organic carboxylic acid: U.S. Pat. No. 4,394,299, U.S. Pat. No. 4,415,479, and U.S. Pat. No. 4,467,110.

The color level of purified terephthalic acid is generally evaluated either by measuring the optical density of a solution of the purified terephthalic acid or by determining the b* value of the solid purified terephthalic acid. The optical density of purified terephthalic acid is measured as the absorbance of light at 340 nm nanometers in its basic solution in a solvent such as sodium hydroxide or ammonium hydroxide.

The measurement of the b* value of a solid on the Hunter Color Scale is described in Hunter, *The Measurement of Appearance*, Chapter 8, pp. 102–132, John Wiley & Sons, N.Y., N.Y. (1975), and in Wyszecki et al., *Color Science, Concepts and Methods, Quantitative Data and Formulae*, 2d Ed., pp. 166–168, John Wiley & Sons, N.Y., N.Y. (1982). A spectrophotometer can be used to measure the spectrum of visible light reflected from a sample of the solid acid, from which spectrum the b* value of purified terephthalic acid can be determined.

The use of b* values as a measure of quality for aromatic dicarboxylic acids purified by catalytic hydrogenation is described in, for example, Schroeder et al., U.S. Pat. No. 4,892,972, Schroeder, U.S. Pat. No. 4,937,378, Bartos et al., U.S. Pat. No. 5,616,792, and Rosen et al., U.S. Pat. No. 5,756,833, the disclosures of which are incorporated herein by reference.

BRIEF SUMMARY OF THE INVENTION

The present invention is directed to a process for reducing the visible color of a crude aromatic dicarboxylic acid containing colored contaminants that comprises: forming an aqueous ammonia solution of the crude aromatic dicarboxylic acid, and contacting the aqueous solution with hydrogen in a reactor in the presence of a heterogeneous metal-containing catalyst that includes a noble metal and a support. The process is carried out under conditions of temperature, pressure, and contact time effective to reduce the visible color of the aromatic dicarboxylic acid.

DETAILED DESCRIPTION OF THE INVENTION

The present invention is a process for decolorizing an aromatic dicarboxylic acid contaminated by impurities having visible color. An aqueous ammonia solution of the diacid, which preferably is crude terephthalic acid (CTA), is contacted with hydrogen in the presence of a heterogeneous metal catalyst. The molar ratio of the diacid to ammonia is preferably about 0.5 to about 10, more preferably about 1.5 to about 2.5. The heterogeneous metal catalyst preferably comprises a noble metal on a support. Preferred metals include platinum, palladium, ruthenium, rhodium, and combinations thereof, palladium and ruthenium being more preferred. Suitable supports include carbon, titania, zirconia, silica, and silicon carbide, carbon being preferred. The metal is loaded on the support at a preferred concentration of about 0.1 wt. % to about 10 wt. %, more preferably about 0.5 wt. % to about 1 wt. %.

In accordance with the present invention, a solution of CTA in aqueous ammonia is contacted with hydrogen in the presence of a heterogeneous catalyst in a reactor that may be, for example, an autoclave, a batch reactor, a continuously-stirred tank reactor (CSTR), a series of CTRS's, or a fixed-bed reactor. The reaction temperature is preferably about 80° C. to about 220° C., more preferably about 120° C. to about 180° C. The reaction pressure is preferably about 50 psig to about 1000 psig, more preferably about 100 psig to about 200 psig. The hydrogen partial pressure is about 1 Kg/cm to about 20 Kg/cm, as calculated at 150° C. The contact time of the CTA-ammonia solution with hydrogen and the catalyst in the reactor is preferably about one minute to about 2 hours, more preferably about 0.5 hour to about one hour. The formation of the CTA-ammonia solution and its hydrogenation may be carried out either in the same reactor or in separate reactors.

Following hydrogenation, the solution is filtered to remove the catalyst, and the filtrate is heated at an elevated temperature, preferably about 150° C. to about 300° C., to evaporate water and drive off ammonia. If desired, the water and ammonia can be recycled to the reactor or other vessel for further use.

Based on its b* value compared to that of the starting crude acid, the residual powder of dicarboxylic acid obtained by the process of the present invention is of a sufficiently improved color to make it suitable for use as a reactant in the preparation of high quality PET, without the expense and waste associated with a recrystallization step.

This invention can be further illustrated by the following examples, although it will be understood that these examples are included merely for purposes of illustration and are not intended to limit the scope of the invention unless otherwise specifically indicated.

EXAMPLE 1 (COMPARATIVE)

The spectrum of a sample of crude terephthalic acid (CTA) prepared by the direct oxidation of p-xylene by oxygen is measured by a Hunterlab UltraScan XE Spectrocolorimeter in a reflectance mode and used to determine a b* value of 4.05 on the CIE L*, a*, b* Color Scale.

To a 300 cc stainless steel autoclave containing 20 g of carbon granules in a stainless steel catalyst basket is added 120 g of distilled deionized water and 36 g of 29% aqueous ammonia solution, followed by the addition, with agitation, of 30 g of CTA. The autoclave is purged at ambient temperature twice with 10 psig nitrogen and then with 10 psig hydrogen. The autoclave is heated to 150° C. at a heating rate of 10° C./minute and pressurized to 150 psig with hydrogen. After 30 minutes, the autoclave is cooled to ambient temperature and purged with nitrogen. The solution is discharged from the autoclave and filtered to remove carbon fines, and the filtrate is evaporated by heating at 130° C. The residual powder is heated in an oven at 160° C. for one hour. The b* value of this powder is substantially the same as the starting CTA.

EXAMPLE 2

The procedure is similar to that of Comparative Example 1, except that 20 g of 1% Pd/carbon granules (¼") is placed in the stainless steel catalyst basket contained in the autoclave, to which is added 140 g of distilled deionized water and 36 g of 29% aqueous ammonia solution, followed by the addition, with agitation, of 20 g of CTA. Hydrogenation and separation of the treated powder are carried out as described in Comparative Example 1. The b* value determined for this powder is 1.27, a substantial improvement over the b* value for the starting CTA.

EXAMPLE 3 (PROPHETIC)

The procedure is similar to that of Comparative Example 1, except that 20 g of 0.5% Pd/carbon granules (¼") is placed in the stainless steel catalyst basket contained in the autoclave, to which is added 120 g of distilled deionized water and 36 g of 29% aqueous ammonia solution, followed by the addition, with agitation, of 30 g of CTA. Hydrogenation and separation of the treated powder are carried out as described in Comparative Example 1. The b* value determined for this powder is substantially improved over that of the starting CTA.

EXAMPLE 4 (PROPHETIC)

The procedure is similar to that of Comparative Example 1, except that 20 g of 0.5% Pd/carbon granules (¼") is placed in the stainless steel catalyst basket contained in the autoclave, to which is added 120 g of distilled deionized water and 36 g of 29% aqueous ammonia solution, followed by the addition, with agitation, of 20 g of CTA. The autoclave is heated to 150° C. at a heating rate of 10° C./minute and pressurized to 120 psig with hydrogen. After 30 minutes, the autoclave is cooled to ambient temperature and purged with nitrogen. Separation of the treated powder is carried out as described in Comparative Example 1. The b* value determined for this powder is substantially improved over that of the starting CTA.

EXAMPLE 5 (PROPHETIC)

The procedure is similar to that of Comparative Example 1, except that 10 g of 1% Ru/carbon granules (¼") is placed in the stainless steel catalyst basket contained in the autoclave, to which is added 120 g of distilled deionized water and 36 g of 29% aqueous ammonia solution, followed by the addition, with agitation, of 30 g of CTA. The autoclave is heated to 130° C. at a heating rate of 10° C./minute and pressurized to 150 psig with hydrogen. After 30 minutes, the autoclave is cooled to ambient temperature and purged with nitrogen. Separation of the treated powder is carried out as described in Comparative Example 1. The b* value determined for this powder is substantially improved over that of the starting CTA.

EXAMPLE 6 (PROPHETIC)

The procedure is similar to that of Comparative Example 1, except that 20 g of 1% Ru/carbon granules (¼") is placed in the stainless steel catalyst basket contained in the autoclave, to which is added 140 g of distilled deionized water and 36 g of 29% aqueous ammonia solution, followed by the addition, with agitation, of 20 g of CTA. Hydrogenation and separation of the treated powder are carried out as described in Comparative Example 1. The b* value determined for this powder is substantially improved over that of the starting CTA.

The invention has been described in detail with particular reference to preferred embodiments thereof, but it will be understood that variations and modifications can be effected within the spirit and scope of the invention.

What is claimed is:

1. A process for reducing the visible color of a crude aromatic dicarboxylic acid mixture containing colored contaminants, said process comprising:
    forming an aqueous ammonia solution containing said crude aromatic dicarboxylic acid; and
    contacting said aqueous ammonia solution containing said crude aromatic dicarboxylic acid with hydrogen in a reactor in the presence of a heterogeneous metal-containing catalyst comprising a noble metal and a support under conditions of temperature, pressure, and contact time effective to reduce the visible color of said aromatic dicarboxylic acid.

2. The process of claim 1 further comprising:
filtering said solution to remove said catalyst, and heating the filtered solution an elevated temperature to remove ammonia and water, thereby producing a residual solid comprising aromatic dicarboxylic acid having reduced visible color.

3. The process of claim 2 wherein said elevated temperature is about 150° C. to about 300° C.

4. The process of claim 2 further comprising:
determining b* values for each of said crude aromatic dicarboxylic acid and said solid aromatic dicarboxylic acid having reduced color, said b* values being compared to provide a measure of reduction in visible color effected by said process.

5. The process of claim 1 wherein said crude aromatic dicarboxylic acid is crude terephthalic acid.

6. The process of claim 1 wherein said heterogeneous metal-containing catalyst comprises a noble metal selected from the group consisting of platinum, palladium, ruthenium, rhodium, and combinations thereof.

7. The process of claim 6 wherein said metal is palladium or ruthenium.

8. The process of claim 1 wherein said heterogeneous metal-containing catalyst comprises a support selected from the group consisting of carbon, titania, zirconia, silica, and silicon carbide.

9. The process of claim 8 wherein said support is carbon.

10. The process of claim 1 wherein said heterogeneous metal-containing catalyst comprises said metal loaded on said support at a concentration of about 0.1 wt. % to about 10 wt. %.

11. The process of claim 10 wherein said heterogeneous metal-containing catalyst comprises said metal loaded on said support at a concentration of about 0.5 wt. % to about 1 wt. %.

12. The process of claim 1 wherein said temperature is about 80° C. to about 220° C.

13. The process of claim 12 wherein said temperature is about 120° C. to about 180° C.

14. The process of claim 1 wherein said pressure is about 50 psig to about 1000 psig.

15. The process of claim 14 wherein said pressure is about 100 psig to about 200 psig.

16. The process of claim 1 wherein said contact time is about one minute to about 2 hours.

17. The process of claim 16 wherein said contact time is about 0.5 hour to about one hour.

18. The process of claim 1 wherein said ammonia and said crude dicarboxylic acid are present in said solution in a molar ratio of about 0.5 to about 10.

19. The process of claim 18 wherein said ammonia and said crude dicarboxylic acid are present in said solution in a molar ratio of about 1.5 to about 2.5.

20. The process of claim 1 wherein said forming said aqueous ammonia solution containing said crude aromatic dicarboxylic acid and said contacting said aqueous ammonia solution with said hydrogen are carried out in the same reactor.

21. The process of claim 1 wherein said forming said aqueous ammonia solution containing said crude aromatic dicarboxylic acid and said contacting said aqueous ammonia solution with said hydrogen are carried out in separate reactors.

22. The process of claim 2 wherein said ammonia and/or said water are recycled.

* * * * *